United States Patent [19]
Eisenbach et al.

[11] Patent Number: 5,902,576
[45] Date of Patent: May 11, 1999

[54] ANTITUMOR PHARMACEUTICAL COMPOSITION COMPRISING IL-6 TRANSFECTED CELLS

[75] Inventors: Lea Eisenbach, Rehovot; Angel Porgador, Rishon Lezion; Michael Feldman; Michel Revel, both of Rehovot, all of Israel

[73] Assignee: YEDA Research and Development Co. Ltd. at Weizmann Institute of Science, Rehovot, Israel

[21] Appl. No.: 08/430,248

[22] Filed: Apr. 28, 1995

Related U.S. Application Data

[63] Continuation of application No. 07/964,719, Oct. 22, 1992, abandoned.

[51] Int. Cl.⁶ .............................. A61K 48/00; C12N 5/00
[52] U.S. Cl. ..................... 424/93.21; 514/44; 435/325; 435/366
[58] Field of Search .................. 514/44; 424/93.21; 435/240.1, 325, 366

[56] References Cited

U.S. PATENT DOCUMENTS 5,188,828  2/1993  Goldberg et al. ........................ 514/8

FOREIGN PATENT DOCUMENTS

| | | |
|---|---|---|
| 0220574 | 10/1986 | European Pat. Off. . |
| 0326120 | 1/1989 | European Pat. Off. . |
| 3922444A1 | 10/1991 | Germany . |
| 9205262 | 4/1992 | WIPO . |
| WO92 05262 | 4/1992 | WIPO ............................ C12N 15/85 |
| WO93 06867 | 4/1993 | WIPO ............................ A61K 48/00 |

OTHER PUBLICATIONS

Vieweg et al (1995) Cancer Investigation 13, 193–201.
Zilberstein et al., The EMBO Journal, vol. 5, No. 10, pp. 2529–2537 (1986).
Black et al, Endocrinology, vol. 128 No. 5, pp. 2657–2659 (May 1991).
Mullen et al, Cancer Res, vol. 52, pp. 6020–6024 (Nov. 1, 1992).
Scala et al, J. Exp. Med. vol. 172 pp. 61–62 (Jul. 1990).
Mulé et al., J. Exp. Med., vol. 171 pp. 629–636 (Mar. 1990).
Porgador et al., "Interleukin 6 gene transfection into Lewis lung carcinoma tumor cells suppresses the malignant phenotype . . ." *Cancer Research*, 52:3679–3686 (1992).
Russell, SJ. "Lymphokine gene therapy for cancer" *Immunotherapy Today*, vol. 11, No. 6, pp. 196–200 (1990).
Revel, M., Experientia 45:549–55 (1989).
Kishimoto, T., Blood 74:1–10 (1989).
Sehgal, P., Proc. Soc. Exp. Biol. Med. 195:183–191 (1990).
Eisenbach, L., et al., Int. J. Cancer 34:567–573 (1984).
Plaksin, D., et al., Proc. Natl. Acad. Sci. USA 85:4463–4467 (1988).
Southern, P., et al., J. Mol. Appl. Genet. 1:327–341 (1982).
Watanabe, Y., et al., Proc. Natl. Acad. Sci. USA 86:9456–9460 (1989).
Gansbacher, B., et al., Cancer Res. 50:7820–7825 (1990).
Fearon, E., et al., Cell. 60:397–403 (1990).
Ley, V., et al., Eur. J. Immunol. 21:851–854 (1991).
Gansbacher, B., et al., J. Exp. Med. 172:1217–1224 (1990).
Tepper, R., et al., Cell. 57:503–512 (1989).
Chirgwin, J. et al., Biochemistry 18:5294–5298 (1979).
Ozato, K. et al., J. Immunol. 126:317–321 (1981).
Eldar H., et al., J. Biological Chemistry. 265:13290–13296 (1990).
Gilboa, E., et al., BioTechniques. 4:504–512 (1986).
Markowitz, D., et al., J. Virology 62:1120–1124 (1988).
Markowitz, D., et al., J. Virology 167:400–406 (1988).

*Primary Examiner*—Deborah Crouch
*Attorney, Agent, or Firm*—Kohn & Associates

[57] ABSTRACT

An anti-tumor pharmaceutical composition includes cells into which a gene encoding human IL-6 has been inserted. A method of treatment of a patient suffering from cancer to prevent and/or inhibit the development of metastases by administering to the patient the anti-tumor pharmaceutical composition including the above mentioned cells.

14 Claims, 7 Drawing Sheets

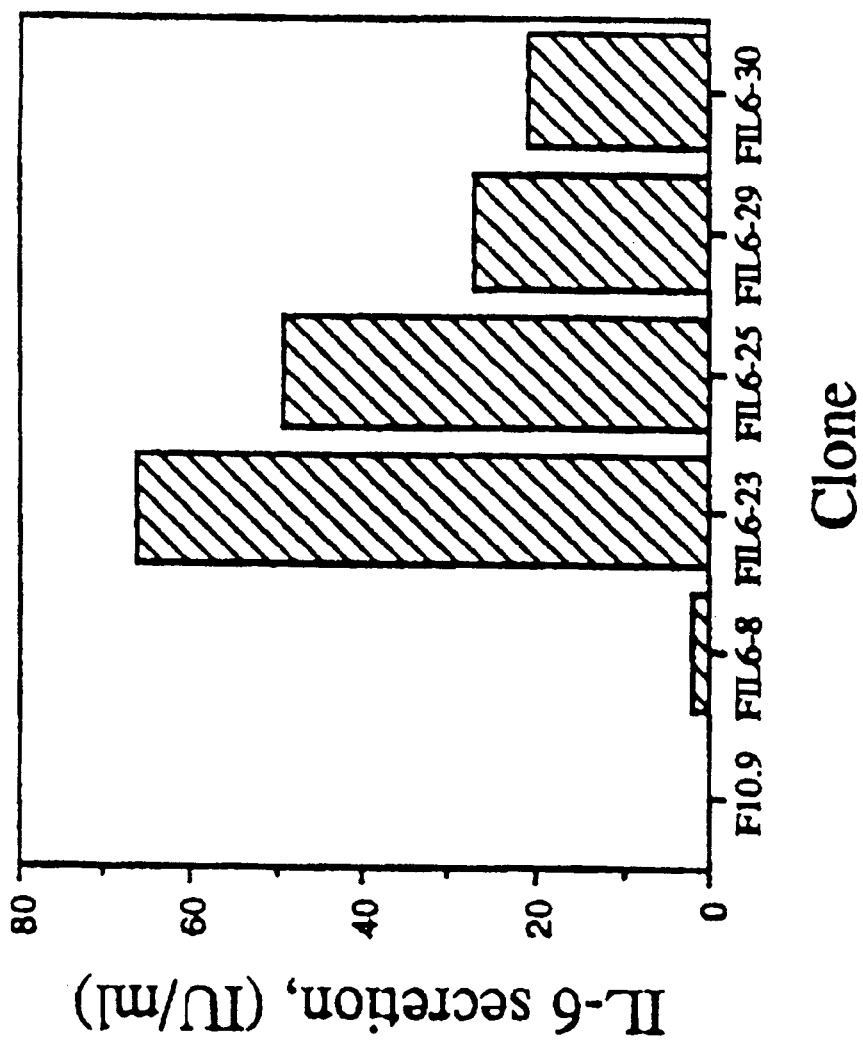
Figure 8 IL-6 secretion by F10.9 and F10.9 IL6- Supernatants were tested by a bio-assay using the IL-6 dependent B9 line (see methods). For collection of supernatants, cells were seeded at $0.5 \times 10^6$ cells per 100mm plate and supernatant was collected 3 days later

ANTITUMOR PHARMACEUTICAL COMPOSITION COMPRISING IL-6 TRANSFECTED CELLS

This is a continuation of application Ser. No. 07/964,719 filed on Oct. 22, 1992 now abandoned.

FIELD OF THE INVENTION

The present invention relates to cellular vaccines for immunotherapy vaccines for immunotherapy of metastases. In particular, the present invention relates to the use of Interleukin-6 transfected tumor cells, after inactivation, as a vaccine for the prevention and inhibition of the development of cancerous metastases.

BACKGROUND OF THE INVENTION

Interleukin-6 (IL-6) is a multifunctional cytokine that plays an important role in the regulation of immune responses, such as stimulation of differentiated functions of B and T lymphocytes, enhancement of hematopoiesis and production of mature myeloid cells and megakaryocytes, and induction of liver acute phase proteins (for review, see refs. 1–3). It has been shown that IL-6, alone or in combination with other cytokines, also acts as a differentiation inducing factor and as a growth inhibitor of certain malignant cell types.

Experiments in vitro showed that the growth of human breast carcinoma lines MCF-7, SK-BR3, T47D and ZR-75.1 was inhibited by human recombinant IL-6 (rIL-6). In murine and human myeloid leukemia lines, human rIL-6 induced terminal differentiation and growth arrest and in fresh leukemic cells isolated from acute myeloid leukemia (AML) patients, treatment with human rIL-6 increased the proportion of cells with a differentiated phenotype. In vivo experiments using FBL-3 erythroleukemia showed that administration of high does human rIL-6 induced a strong anti-tumor CTL activity that cured the tumor-bearing mice. Experiments with several moderately immunogenic, metastatic murine sarcoma lines (MCA 105,106,203) and a colon carcinoma line MC-38 showed that systemic administration of human rIL-6 reduced substantially the number of metastatic lesions.

The Lewis lung carcinoma (3LL) clone D122 is low-immunogenic and high-metastatic in syngeneic C57BL/6 mice. These cells express low levels of H-2K$^b$ transfectants while elevating their immunogenicity (5). Experiments by the inventors have shown that administration of human rIL-6 through various protocols to mice inoculated intravenously or intra-footpad with D122 cells did not affect the malignancy of tumor cells (unpublished results). These observations can be explained either by insensitivity of D122 cells to direct or indirect (via the immune system) effects of IL-6, or by problems involved in the administration procedure in vivo such as short half-life and insufficient local levels at the tumor site of the systemically injected cytokine. It would be highly desirable to produce IL-6 constitutively in vivo and thus overcome the limitations of the systemic administration of IL-6.

SUMMARY OF THE INVENTION

The present invention provides an anti-tumor vaccine, particularly for the prevention and inhibition of metastases, comprising cells into which a gene encoding human IL-6 has been inserted. The cells are preferably tumor cells from the patient to be vaccinated and are inactivated before administration.

The invention also provides a method for the preparation of such vaccines and, in another aspect, it relates to a method of treatment of a patient suffering from a tumor in order to prevent or inhibit metastases, which comprises administration of a vaccine according to the invention.

BRIEF DESCRIPTION OF THE DRAWINGS

FIG. 2(a) shows the levels of IL-6 secretion in the medium as measured by ELISA assays.

FIG. 2(b) shows growth inhibition of IL-6 transfectants compared to parental D122 and to negative transfectant DIL6-4.

FIG. 2(c) shows direct RIA analysis of cell surface expression of H-2k$^b$ and H-2D$^b$ antigens.

FIG. 4 shows the results of a clonogenic assay of parental D122 cells and IL-6 transfectants.

FIG. 8 shows a comparison of secretion of the F10.9 IL6-transfectant with the secretion of F10.9 IL6-transduced cells.

GENERAL DESCRIPTION OF THE INVENTION

Figure 1:
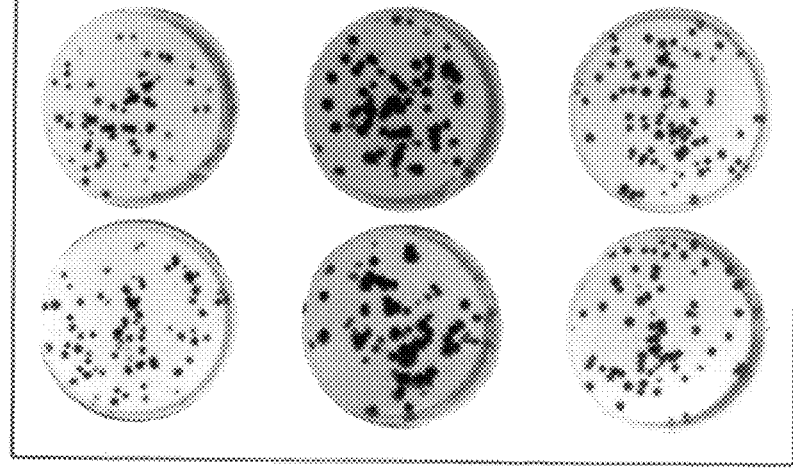
FIG. 1 shows the steady state levels of IL-6(a) and β-actin(b) mRNA transcripts in IL-6 transfects.

It has now been found according to the present invention that malignant cancer cells that have been genetically manipulated to produce IL-6 constitutively may be used as an effective anti-tumor vaccine, particularly to prevent and inhibit the development of metastases. Thus, Lewis lung carcinoma D122 cells were transfected with human IL-6 cDNA linked to a constitutive promoter and the positive transfectants showed reduced malignancy and an elevated immunogencity. The reduction of malignancy seemed a function of growth inhibition of the transfected cells, and of stimulation of host immune responses.

In the antimetastatic immunization according to the invention, the ability of the cancer cells to produce IL-6 is crucial for their efficiency to prevent metastases, and the survival of the cancerous animals was shown to be markedly prolonged as a result of such immunization treatments.

It is further shown in the present invention that the treatment by IL-6 producing cells can be initiated in animals which already have a tumor of palpable size, and the prevention of metastases is thereby achieved.

The anti-tumor vaccines according to the invention comprise cells into which a gene encoding human IL-6 has been inserted, such that there is constitutive production of human IL-6 in vivo. The cells are tumor cells having metastatic competence or having substantially no metastatic competence, or non-tumor cells, such as primary fibroblasts or fibroblast cell lines. They may be derived from the patient to be vaccinated or from a different individual. In a preferred embodiment, these cells are tumor cells, withdrawn from a solid tumor of the patient to be vaccinated.

The human IL-6 gene inserted into the cells is, for example, the IL-6 cDNA which sequence is disclosed in European Patent Application No. EP 0220574. The IL-6 DNA may be inserted into suitable vectors, such as eukaryotic expression vectors or retroviral vectors. A suitable eukaryotic vector is the pSVβ$_2$29 plasmid disclosed in European Patent Application No. EP 0326120 which carries the human IL-6 cDNA under the control of the SV40 early gene promoter. Among the retrovirus vectors, the Molony murine leukemia virus based vectors, e.g., N2, Zip or pZ1, may be used. Once the vector containing the construct has been prepared for expression, the DNA construct may be introduced into the host, e.g. tumor cells, by any of a variety of suitable means, such as calcium phosphate precipitation. The cells will usually be cotransfected with the suitable vector and a vector containing a gene encoding an antibiotic as selectable marker, or the selectable marker gene can be directly linked to the IL-6 DNA sequence. A selectable marker used in the invention is the gene encoding geneticin resistance, comprised within the pSV$_2$-neo vector.

The antibiotic resistant clones are screened for expression of IL-6 mRNA. Positive clones are cultured and positive transfectants, i.e., transfected cells producing IL-6 and secreting it into the medium, are selected and cultured. However, the use of mixtures of positive and negative or low-producing transfectants are also envisaged by the invention. IL-6 transfection of tumor cells of the high metastatic, low immunogenic D122 clone resulted in cells that showed a significantly lower metastatic competence in syngeneic C57BL/6 mice, of both experimental and spontaneous metastasis (Table 2). Two of the three IL-6 transfectants, i.e. the high and moderate IL-6 producers, also showed significantly lower tumorigenicity (i.e. local growth) compared to the parental D122 cells and to the negative IL-6 transfectant (Table 2).

The phenomenon of reduced tumorigenicity after cytokine gene insertion into tumor cells was demonstrated by others for gamma-IFN (7,8), IL-2 (9–11) and IL-4 (12) cytokines. However in the present invention it is shown for the first time that IL-6 gene transfer to tumor cells has an anti-tumor effect. Moreover, this is the only demonstration that a cytokine gene insertion resulted in significant suppression of metastatic growth. Different mechanisms were shown to act with the different cytokine transfectants: gamma-IFN and IL-2 transfectants induced mainly specific cytotoxic T lymphocyte (CTL) activity, while IL-4 induced non-specific anti-tumor activity and granulocyte infiltration. In the case of IL-6 gene transfer to D122, it seems that more than one mechanism is involved in the reduction of tumorigenicity and of metastatic competence.

Figure 2:
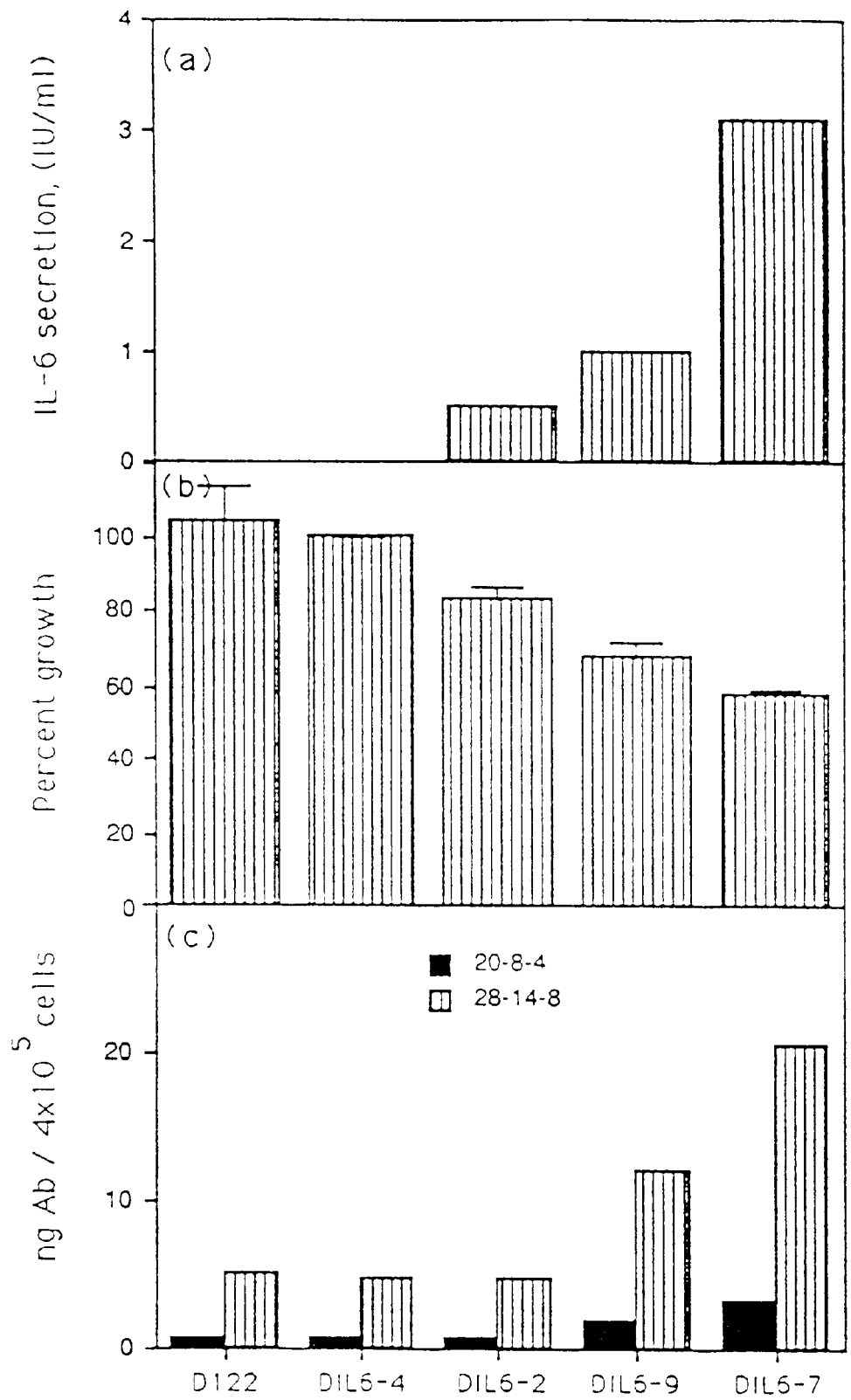
FIG. 2 illustrates the secretion of IL-6 by D122 and IL-6 transfectants using both an ELISA and a bio-assay method.
Figure 3:
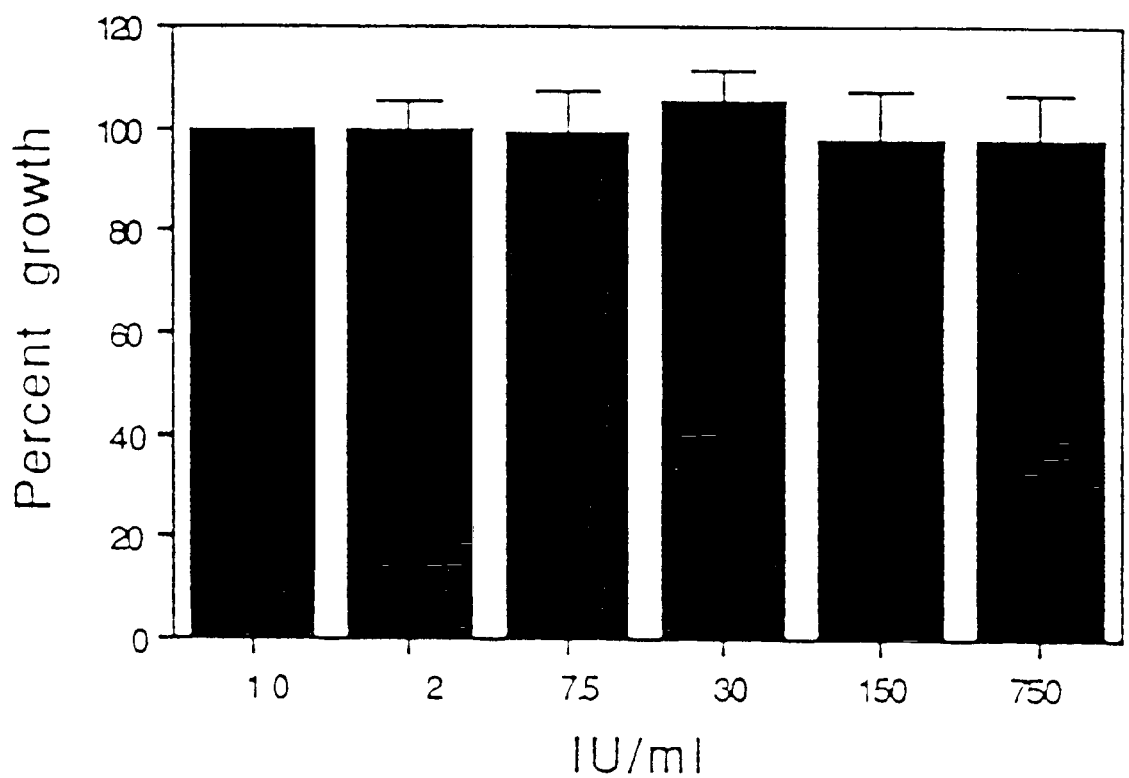
FIG. 3 shows growth of D122 parental cells treated with exogenous human rIL-6 (2–750 IU/ml) as compared to non-treated D122 cells.

The three IL-6 producing transfectants showed growth inhibition in vitro that was directly correlated to the amount of IL-6 production (FIG. 2). Yet the growth inhibition did not seem to be a function of an autocrine effect via secretion of IL-6 into the medium since antibody that neutralized IL-6 activity did not abolish the growth inhibition of the positive IL-6 transfectants (Table 1). Moreover, application of exogenous human rIL-6 in a wide range of concentrations did not cause growth inhibition of D122 cells (FIG. 3). Hence, it appears that the presence of intracellular IL-6 in D122 cells induced a growth inhibitory signal either through a private autocrine loop or by endogenous induction in the tumor cells of a second growth inhibitory factor that is secreted and acts by a classical membrane receptor binding pathway. DIL6-7 and DIL6-9 showed an elevation in MHC class-I expression (FIG. 2c). Yet, here again in accordance with growth inhibition of the transfectants, exogenously applied rIL-6 had no effect on class-I expression of D122 cells.

The inhibition in tumorigenicity and metastasis may be the result of inhibition in proliferation of IL-6 transfectants or other mechanisms are also involved. The observation that the reduction in tumorigenicity is more pronounced in immune-competent mice than in nude mice, and that suppression of metastasis and prolongation of post-amputation survival was observed only in immune-competent mice (Table 3) indicate that mature T-cells do play a significant role in reduction of malignancy. Indeed IL-6 positive transfectants induced higher levels of anti-tumor CTL than did the parental D122 cells (Table 4). This CTL induction could be due to the direct effect of secreted IL-6 on maturation of T cells, or also due to the increased immunogenicity of the tumor cells caused by or also due to the elevation in MHC class-I expression on the high positive IL-6 transfectants (FIG. 2c).

Figure 5:
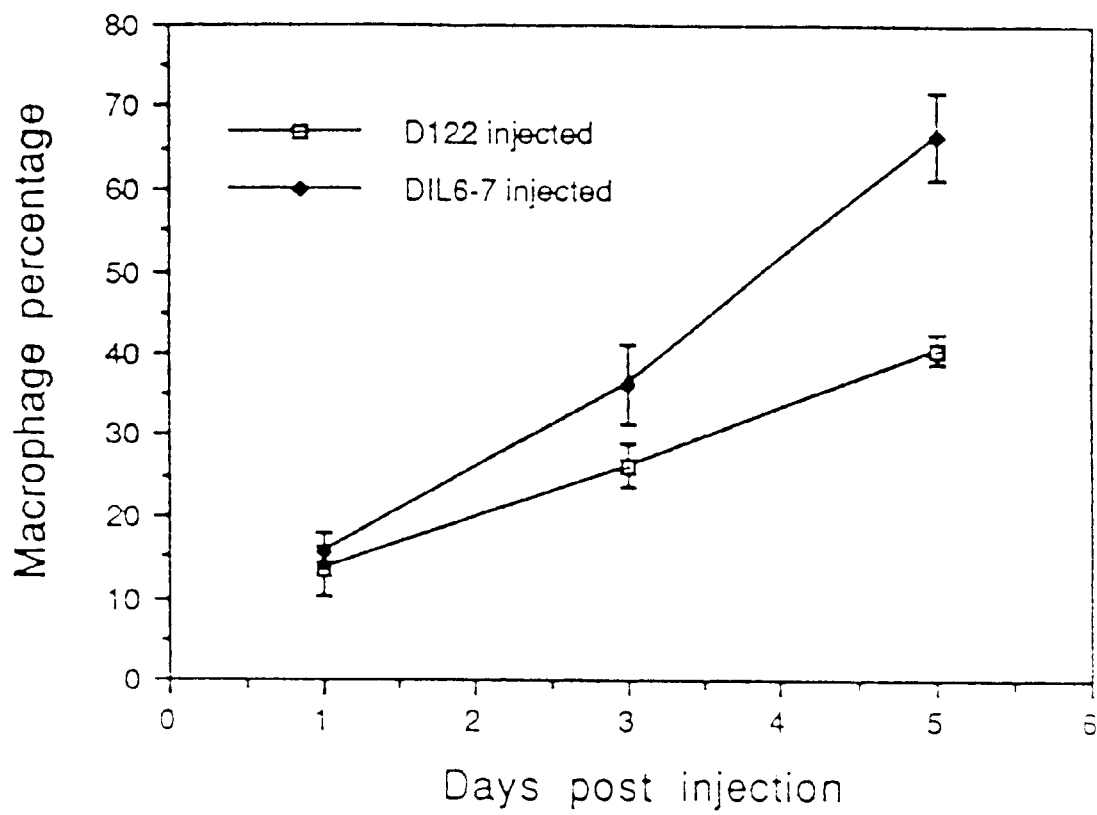
FIG. 5 shows the macrophage percentage in peritoneal exude cells of mice inoculated with $10^7$ irradiated DIL6-7 and D122 cells.
Figure 6:
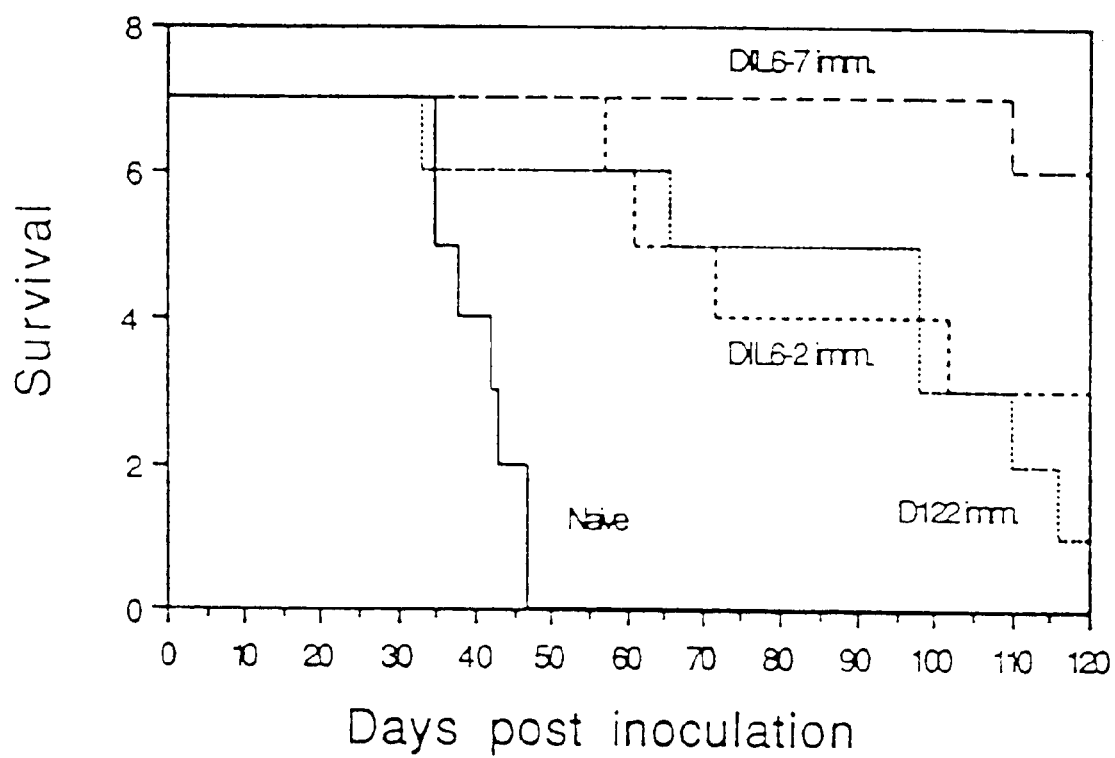
FIG. 6 shows the survival curves of C57BL/6 mice pre-immunized with irradiated and mitomycin-C treated tumor cells and inoculated i.v. with $5 \times 10^5$ living highly-metastatic D122 cells.

Additional support to the involvement of memory-dependent immune mechanisms in the reduced malignancy of IL-6 transfectants derives from protection experiments. FIG. 6 shows that mice immunized with inactivated high IL-6 producer, DIL6-7, conferred protection against metastatic growth of a subsequent graft of parental cells. It is possible that other, non-specific and memory-independent, immune mechanisms are also involved in the response to IL-6 producing tumor cells. FIG. 5 shows that the localization of peritoneal macrophage in response to i.p. inoculation of inactivated tumor cells was significantly higher when positive IL-6 transfectant was inoculated than when D122 cells were inoculated. These macrophage could be involved in antigen presentation and induction of T helper cells or might manifest tumoricidal activity.

Figure 7:
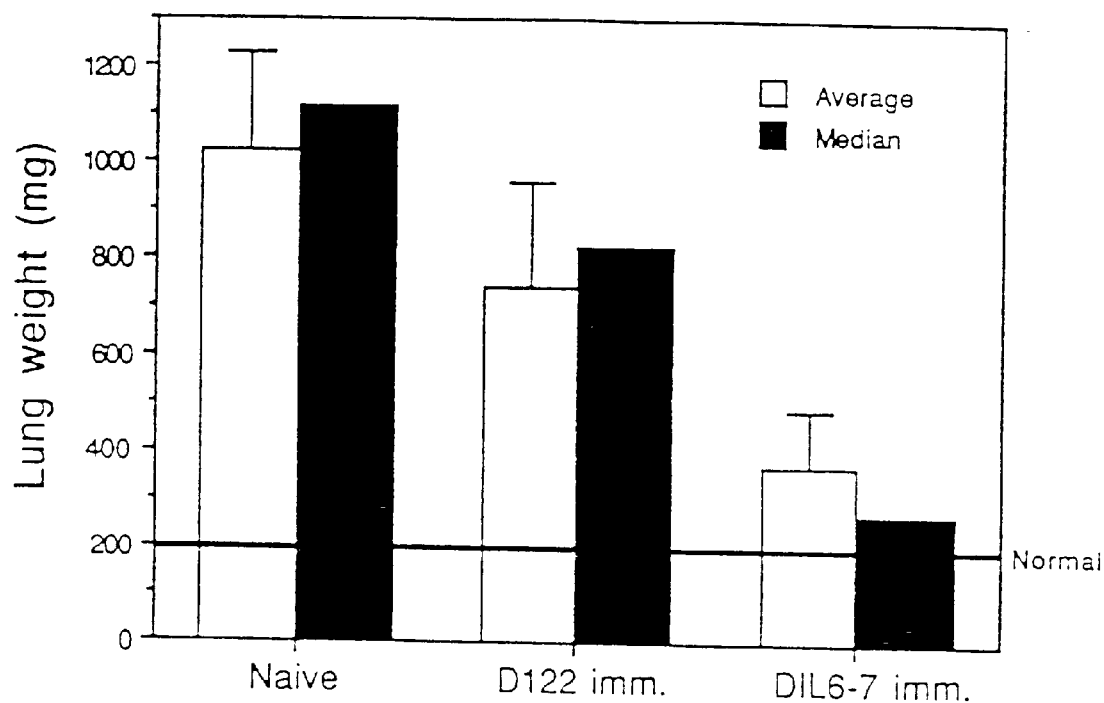
FIG. 7 shows the mean and median metastatic loads of C57bl/6 male mice inoculated with D122 cells and then immunized with D122 or DIL6-7 cells.

In view of the immune responses to IL-6 producing tumor cells, it was tested whether these cells can be used in immunotherapy protocol against metastatic spread of an already established parental D122 tumor. FIG. 7 shows that indeed immunization with inactivated DIL6-7, the high positive IL-6 transfectant, reduced significantly the metastatic growth of D122 cells in tumor bearing mice. Gamma-IFN, IL-2 or IL-4 cytokine transferred tumor cells had been shown to induce protection against subsequent challenge of parental cells or against coinjected parental cells (7–12), yet immuno-therapeutic effects on established parental tumors were not shown for any of the cytokine gene insertion to tumor cells described thus far.

Hence, antimetastatic immunotherapy by cellular vaccines of tumor cells manipulated to express IL-6, either alone or in combination with genes of MHC or of other cytokines, may be provided according to the invention. The use of gene insertion, as distinct from systemic administration of IL-6, may result in optimal functional levels of IL-6 primarily at the site of the desired tumor-immune cell interaction.

The present invention, for the first time, provides a successful immunoprotection in cancer therapy. All types of solid tumors can be treated, including lung, colon, breast, ovary, pancreas, liver, stomach, kidney, or prostate cancers, melanoma and lymphomas.

The human IL-6 transfected cells will preferably be inactivated or attenuated by gamma or X-irradiation and/or treatment with mitomycin C, by methods well-known in the art, for their use in the preparation of anti-tumor vaccines.

The present invention provides anti-tumor vaccines comprising the IL-6 transfected cells which produce IL-6 constitutively, and optionally a pharmaceutically acceptable carrier or diluent. The vaccines according to the invention can be administered by any of a number of means and routes known in the art. For example, administration may be by subcutaneous, intravenous, intraarterial, intramuscular or intraperitoneal injection, or by infusion. The dosage administered will be dependent upon the condition of the patient and the severity of the disease. Antitumor vaccines comprising $10^6$ to $10^9$ cells, preferably $10^7$ to $10^8$ cells, most preferably $10^7$ cells, at a dose, are administered to a cancer patient according to the invention. The treatment will comprise several doses at intervals of 5–7 days each, according to the necessity.

The human IL-6 transfected cells according to the invention will be used in a method for the treatment of a patient suffering from cancer, e.g. a malignant solid tumor, for prevention and/or inhibition of the development of metastases, which method comprises the steps of: a) removing tumor cells from the patient by biopsy or surgery; b) dispersing the cells in a medium; c) inserting into said cells a vector comprising the human IL-6 gene; d) optionally selecting the positive transfectants that secrete IL-6 to the medium; e) inactivating the transfectants by gamma- or X-irradiation and/or treatment with mitomycin C; and f) administering an effective amount of the inactivated human IL-6 transfected producing cells into said patient, whereby an anti-tumor immune response in said patient is induced, thus preventing and/or inhibiting tumor metastases.

The invention will now be illustrated by the following examples without limiting it thereto. In the examples the following Experimental Methods were employed:

EXPERIMENTAL MATERIALS AND METHODS a. Mice: Eight to twelve-week old C57BL/6 mice (Jackson Laboratories, Bar Harbor, Ma.). CD1 Nu/Nu mice bred in the Weizmann Institute of Science, Rehovot, Israel.

b. Tumor cells: Cells of high metastatic, low immunogenic D122 clones of the 3LL carcinoma and of the B-16 melanoma, respectively, of a C57BL/6 ($H-2^b$) origin.

c. Cell cultures: Cells were maintained in Dulbecco's modified Eagle's medium (DMEM), supplemented with 10% heat inactivated fetal calf serum (FCS) (Biological Industries, Beth Haemek, Israel, Lot. No. 488908), 2 mM glutamine, 1 mM non-essential amino acids, 1 mM sodium pyruvate and 0.4% combined antibiotics. FNO.9, D122 and IL-6 gene transferred cells were free of mycoplasma as tested by a mycotrim TC test (Hana Biologics, Inc., Alameda, Calif.).

d. Plasmids: The $psV\beta_2 29$ vector containing a 1.2 kilobase (kb) human IL-6 cDNA fragment with the entire coding sequence cloned into pSVE3 plasmid, downstream from the SV40 early gene promoter was used for transfection. The preparation of the $PSV\beta_2 29$ vector is described in the European Patent Application published under No. EP 326120. A $psV_2$neo vector, containing the gene encoding geneticin resistance (6), was cotransfected with the IL-6 plasmid.

e. DNA transfection: Twenty micrograms of IL-6 plasmid and 2 μg of neo plasmid were transfected into $5 \times 10^5$ D122 or F10.9 cells by the calcium phosphate technique. Selection was performed in medium containing 400 μg/ml geneticin analogue, G418 (Gibco). Transfected clones were maintained in medium containing 130 μg/ml G418.

f. pZL; Retroviral expression vector for cytokine gene transfer: pZL (*r1*) was kindly given by Dr. Eta Livneh, Weizmann Institute. The vector is derived from the Molony murine leukemia virus (Mo-MLV) and contains MO-MLV non-coding sequences i.e. the LTRs, ψ-packaging signal and other Mo-MLV regulatory sequences, bacterial neomycin-resistance gene (neo gene), and PBR sequences including the origin of replication. pZL also contains the SV40 early gene promoter upstream to the neo gene and thus neo gene is transcribed by this promoter. A 1.2 kbp, ClaI digested, DNA fragment encoding the entire coding region of the human IL-6 cDNA as well as part of the 3' untranslated region including the poly(A) addition signal was obtained from $pSV\beta_2 29$ vector and cloned into the unique XhoI site of the pZL downstream to the 5' LTR. In this vector (pZL-IL6) IL-6 cDNA is transcribed by the 5' LTR and neo gene is transcribed by the SV40 promoter.

g. Generation of virus stocks. Retroviral constructs were converted to the corresponding virus using helper-free packaging cell lines by the 'trans-infection' method (*r2*) in which vector DNA was transfected into the ecotropic packaging cell line, E86 (*r3*) (kindly given by Dr. A. Bank, Columbia University, New York), and two days later a 24 hour virus containing supernatant of the transiently transfected E86 cells was harvested and used for transduction of AM12 (*r4*) cells (kindly given by Dr. Arthur Bank). Colonies of transduced AM12 cells were isolated by G418 selection and expanded to cell lines, and cell free supernatants were tested for the presence of virus. Supernatants of cell lines secreting high titer of virus were used to infect tumor cells.

h. Retroviral transduction of tumor cells. $5 \times 10^4$ F10.9 cells were seeded in 60 mm plates. Twelve hours later, medium was removed and 3 ml of undiluted virus containing supernatants or dilutions of 1/10 to $1/10^7$ of supernatants were added to plates in the presence of 8 μg/ml polybrene (Sigma). Four to six hours later supernatants were removed and standard medium was added to the plates for 24 hours and then replaced by selection medium containing 800 μg/ml geneticin analogue, G418 (Gibco). Neo-resistant colonies were isolated and screened for expression of the transferred gene. F10.9 transduced cells were grown in maintenance medium containing 260 μg/ml G418.

i. RNA blot analysis: Total RNAs were isolated as described by Chirgwin et al. (13), and RNAs were electrophoresed on 1% agarose/2.2M formaldehyde gels, blotted onto nitrocellulose and hybridized in 50% (vol/vol) formamide/10% (wt/vol) dextran sulphate at 42° C. IL-6 CDNA insert and β-actin plasmid were labeled by nick translation.

j. IL-6 detection in supernatants of IL-6 gene transferred cells: IL-6 gene transferred cells and parental tumor cells were plated in 100 mm plates with standard medium (without geneticin), $0.4–0.8 \times 10^6$ cells per plate. Three days later, supernatants were collected. ELISA assay. The IL-6 content of samples were determined by a non-competitive ELISA assay using the monoclonal antibody 34.1 immobilized on a solid phase. The preparation of the monoclonal antibody 34.1 is described in European Patent Application No. EP 326120. The hybridoma 34.1 was deposited with the Collection Nationale des Cultures de Microorganismes—CNCM, Institut Pasteur, Paris, on 14.11.88, under No. I-813. One mg IL-6 corresponds to $10^7$ reference units (IU) determined in comparison to standard 88/514 (National Institute of Biological Standards and Controls, Potters Bar, UK). Bio-assay. The IL-6 dependent murine hybridoma cell line, B9, was used to titrate IL-6 levels. Proliferation of B9 cells in presence of IL-6 containing supernatants was measured by 3H-thymidine uptake.

k. In vitro growth and clonogenic assays. Colorimetric growth assays: D122-IL-6 transfectants were passaged once before assay in standard medium without geneticin, then plated in 24-well costar plates at 5000 or 10000 cells per well in standard medium. Four to five days after plating, cells were fixed with 12.5% glutaraldehyde, stained with 0.1% crystal violet and washed in $H_2O$. The color was extracted in 10% acetic acid, and optical density (570 nm) was measured. For growth assays with anti-IL-6 antibody, 100 neutralizing units/well of 34.1, a monoclonal antibody that neutralizes IL-6 activity, were added on days 1 and 3 to wells of a growth assay. Growth assays of D122 exogenously supplemented with human rIL-6 (produced in Chinese hamster ovary cells, Interpharm Laboratories Ltd. Nes Ziona, Israel) were performed by the same protocol with amounts of IL-6 ranging between 2 to 750 IU/ml. Clonogenic assays. IL-6 transfectants and parental D122 cells were seeded at 100, 200 and 400 cells per 6-well COSTAR plates. Twelve to fourteen days later cells were fixed and stained as in growth assays and colonies were counted. Clonogenic assays of D122 with exogenously supplemented human rIL-6 were performed by the same protocol with amounts of IL-6 ranging between 1 to 1500 IU/ml.

l. Detection of cell-surface antigens.: Monoclonal antibodies 20-8-4 (anti H-2$K^b$) and 28-14-8 (anti -2$D^b$) were purified from ascites fluids on protein A-sepharose. For direct radioimmunoassays, purified antibodies were labeled with $Na^{125}I$ by chloramine T. Cell suspensions ($4 \times 10^5$ cells in 0.1 ml PBS per tube) were incubated with 0.5 ug of labeled antibodies in triplicate in bovine serum albumin-precoated tubes for 2 hours at 0° C. Cells were washed four times with PBS/0.02% sodium azide, and monitored in a gamma-scintillation counter.

m. Tumor growth and spontaneous metastasis: Mice, 7–10 in each experimental group, were inoculated intrafootpad (i.f.p.) with $2 \times 10^5$ cells per mouse. Local tumor growth was determined by measuring the footpad diameter with calipers. To measure lung metastasis, the tumor-bearing leg was amputated (below the knee) when the tumor reached 8–9 mm in diameter and the mice were sacrificed 26–29 days post amputation or survival was monitored. The legs were assessed for metastatic load by weighing.

n. Experimental metastasis: Mice in each experimental group were inoculated intravenously (i.v.) with $5 \times 10^5$ D122 or $5 \times 10^4$ f10.9 tumor cells. Mice were sacrificed 30–35 days post inoculation or survival was monitored. Metastatic load was assayed by weighing the lungs.

o. Immunizations: Mice were immunized intraperitoneally (i.p.) three times at 7-day intervals, with $2 \times 10^6$ cells that had been irradiated (5000 rad) and treated with mitomycin-C (80 mg/5–$10 \times 10^6$ cells/ml for 1 hour at 37° C.). Ten days after the third booster injection, the mice were challenged i.v. with D122 cells ($5 \times 10^5$), or spleens were removed for in vitro cytotoxicity assays.

p. In vitro cytotoxicity assay: Spleen cells were taken from immunized mice 10 days after the third booster and restimulated in vitro on monolayers of irradiated tumor cells (5000 rad) previously treated with mitomycin-C (80 mg/ml) in RPMI medium supplemented with 10% FCS, 2 mM glutamine and $2 \times 10^{-5M}$ β-mercaptoethanol for five days. Viable lymphocytes were separated by lymphoprep centrifugation (Cedarlane, Ontario, Canada) and admixed at different ratios with 5000 [$^{35}$S]-L-methionine labeled target cells in U-shaped microtiter wells. The plates were incubated for 16 hours at 37° C. Cultures were terminated by centrifugation at 300×g for ten minutes at 4° C. and 100 μl of supernatants were assayed in a gamma-scintillation counter. Percent specific lysis was calculated at follows:

$$\frac{\text{Experimental }[^{35}S]\text{ release} - \text{Spontaneous release}}{\text{Maximum release} - \text{Spontaneous release}} \times 100$$

Maximal release was determined by solubilization of target cells in 0.05M NaOH.

q. Intraperitoneal recruitment of macrophage following injection of tumor cells: $10^7$ irradiated (10000 rad) D122 or DIL6-7 cells were injected i.p. to C57BL/6 mice. Peritoneal exudates were aspirated on days 1, 3 and 5 post injection. To assess the levels of macrophage recruitment to the peritoneal cavity, a cytochemical analysis for non-specific esterases was performed with a-naphthyl butyrate according to the method of Kosky. The method allows to identify strained macrophage in fixed smears whereas lymphoid populations and erythrocytes are unstained. Residual tumor cells could be identified by their large size and smooth nucleus, and were omitted from the count.

r. Immunotherapy: Mice were injected i.f.p. with $2 \times 10^5$ D122 cells. Starting on day 11 after injection, when palpable tumors could be detected, the mice were immunized weekly, six times, with inactivated $2 \times 10^6$ tumor cells (mitomycin-C treated as described) i.p. or with phosphate buffered saline (control group). During immunizations, primary tumors in the footpad were amputated when they reached 8–9 mm diameter. Mice were sacrificed 26 days post amputation and lungs were weighed.

EXAMPLE 1

Transfection of IL-6 cDNA into D122 cells. D122 cells were cotransfected with pSVβ29 plasmid which carries a human IL-6 cDNA under the control of the SV40 early gene promoter, and with pSV2-neo plasmid as described in method (e) above. Twenty neo-resistant clones were screened for expression IL-6MRNA. The RNAs were prepared by the method of Chirgwin and electrophoresed as described in method (f) above. In FIG. 1a, the expression of the transcript in the different transfectants is shown after the blot was hybridized to a labeled IL-6 cDNA insert, washed in 0.1×SSC (150 mM NaCl, 15 mM Na citrate, pH 7.0) at 50° C. and exposed to autoradiography for two days. In FIG. 1b, the blot was hybridized to a labeled β-actin plasmid, washed in 0.05×SSC at 65° C. and exposed for one day.

Three positive clones (DIL6-9, DIL6-7 and DIL6-2) and one negative (DIL6-4) clone were chosen. FIG. 1 shows the expression of the 1.2 kb IL-6 transcript of the negative and positive IL-6 transfectants. Among the positive transfectants, DIL6-7 shows the highest steady state levels of IL-6 mRNA, DIL6-9 expresses moderate levels and DIL6-2 shows the lowest levels of IL-6 mRNA. DIL6-4, the negative transfectant, does not express IL-6 mRNA. An unprocessed transcript (¯3.2 kb) can also be observed in DIL6-2,7,9 lanes.

Secretion of IL-6 was tested using both an ELISA and a bio-assay as described in method (g) above. FIG. 2(a) shows the levels of IL-6 secretion as measured by ELISA assays in the supernatants. For collection of supernatants, cells were seeded at $0.8 \times 10^6$ cells per 100 mm plate and supernatant was collected three days later. Secretion of DIL6-2, 9 was calculated from supernatants concentrated by an Amicon 8400 using a 10 KD filter. The secretion levels were correlated with the levels of IL-6 mRNA transcript and ranged between 0.5–3.1 IU/ml in supernatants of positive transfectants. The negative transfectant, DIL6-4, and parental D122 cells did not secrete IL-6 to the medium. Bio-assays confirmed these results, however, IL-6 levels in supernatants of the high and moderate IL-6 transfectants (DIL6-7 and DIL6-9, respectively) were significantly higher than in supernatants of the low positive IL-6 transfectant, DIL6-2 (not shown).

EXAMPLE 2

In vitro properties of parental D122 cells and of IL-6 transfectants

Growth inhibition—To test whether IL-6 production affects growth in vitro of the positive transfectants, growth assays were performed both by cell counting in a hemocytometer and by a calorimetric assay using crystal violet. FIG. 2($b$) shows growth inhibition of IL-6 transfectants compared to negative transfectants DIL6-4 and to parental D122 cells, carried out as in method (h) above. The results are the average of four different calorimetric assays. Growth inhibition of 43%, 32% and 17% were observed for DIL6-7, DIL6-9 and DIL6-2, respectively, as compared to the negative transfectant DIL6-4, which grew similarly to the parental D122 cells (all clones were free of mycoplasma, see methods). These growth differences were statistically significant as shown in a representative experiment, summarized in Table 1.

TABLE 1

In vitro growth and clonogenic properties of D122 Cells and IL-6 transfectants

| Clones | Growth without antibody (O.D.) | | Growth with antibody (O.D.) | Number of Colonies |
|---|---|---|---|---|
| | X ± S.D. | P | X ± S.D. | X ± S.D. |
| D122   | 1.11 ± 0.09 | 0.10       | 1.07 ± 0.04 | 87.2 ± 12.2 |
| DIL6-4 | 1.19 ± 0.10 | —          | 1.16 ± 0.08 | 89.4 ± 12.5 |
| DIL6-2 | 0.97 ± 0.04 | $<10^{-4}$ | 0.97 ± 0.07 | 83.0 ± 7.5  |
| DIL6-9 | 0.77 ± 0.04 | $<10^{-6}$ | 0.78 ± 0.04 | 82.5 ± 10.1 |
| DIL6-7 | 0.61 ± 0.03 | $<10^{-6}$ | 0.62 ± 0.07 | 85.6 ± 12.0 |

Growth assay of D122 and IL-6 transfectants in the absence or presence of 34.1, a monoclonal antibody which neutralizes human IL-6. Assays were done as described in method (h) above. T-test was performed on the arithmetic means of optical densities of D122 cells and IL-6 transfectants growing in the absence of antibody. Clonogenic assays on D122 and IL-6 transfectants were done as described in the method (b) above. Interestingly, addition of exogenous human rIL-6 at levels from 2 to 750 IU/ml did not affect the in vitro growth of parental D122 cells, as compared to non-treated D122 cells. FIG. 3 shows the results of a summary of four growth assays. To test whether the growth inhibition of the positive IL-6 transfectants is due to IL-6 in the medium, growth tests were performed in the presence of the monoclonal anti-IL-6 antibody 34.1.

Table 1 shows a representative experiment. No differences were observed in the pattern of growth inhibition of the transfectants that grew in the presence or absence of the antibody. To test whether the observed growth inhibition of the transfectants was more pronounced at low cell density, colony formation was assayed as in method (h) above by seeding 200 cells per well in 6-well costar plates and counting number of colonies twelve days later, after fixing and staining the cells. The number of growing colonies was similar among the negative and positive transfectants and the parental D122 cells (Table 1), but the size of the colonies of IL-6 producing transfectants DIL6-7 and DIL6-9 was smaller as compared to colonies of parental D122, as shown in FIG. 4, in which two representative wells for each clone are shown. The size of individual cells as observed by a light microscope and by measurement of forward scattering in the Fluorescence Activated Cell Sorter (FACS) was similar among all clones. Thus the difference in colony size is attributed to differences in the number of cells forming each colony. Clonogenic assays on D122 cells treated with exogenous rIL-6 at 1 to 1500 IU/ml did not affect the number of size of the colonies (not shown).

D122 cells express low levels of H-2K$^b$ MHC class-I antigen and moderate levels of H-2D$^b$ antigen (4). To test whether IL-6 production affects the MHC class-I expression, radioimmunoassays (RIA) were performed as described in method (i) above using anti H-2K$^b$(20-8-4) and anti H-2D$^b$ (28-14-8) monoclonal antibodies (14). FIG. 2$c$ shows that the moderate IL-6 expressor, DIL6-9, expresses a 2.5–3 fold elevation in H-2Kb, Db antigens and the high IL-6 expressor, DIL6-7, expresses a 4.5 fold elevation of the two antigens. Application of human rIL-6 at a range of 100 to 5000 IU/ml to D122 cells, did not change MHC class-I expression (not shown).

EXAMPLE 3

Tumorigenicity and metastatic phenotypes of IL-6 transfectants

The growth and metastatic competence of IL-6 transfectants in syngeneic C57BL/6 mice were examined as described in method (j) and (k) above. Table 2 shows one of three similar experiments. Primary tumors of the moderate and high IL-6 producers DIL6-2, DIL6-9 and DIL6-7 grew more slowly than the negative transfectant DIL6-4 and parental D122 cells as shown by the number of days until amputation of 8–9 mm tumors. In another experiment, footpads of mice inoculated with DIL6-7 grew to 8–9 mm diameter after 47±2.8 days while footpads of mice injected with DIL6-4 grew to 8–9 mm after 27.6±1.6 days. The low IL-6 producer, DIL6-2, grew similarly or even slightly faster than the negative controls (DIL604 and D122). The differences in growth rate were statistically significant (p<$10^{-3}$ for DIL607,9 compared to DIL6-4 as calculated for the results in Table 2 using a wilcoxon rank sum test).

Spontaneous metastasis was evaluated 26–28 days post-amputation of tumor-bearing footpads when the control groups (DIL604 and D122) died with heavy loads of lung metastases. DIL6-2 showed a low-metastatic phenotype while DIL7-8,9 were non-metastatic at this time. Experimental metastasis was evaluated 30–35 days after i.v. inoculation and showed similar results, i.e., control groups died highly metastatic, DIL6-2 was low metastatic and DIL6-7,9 were non-metastatic.

Survival experiments showed that mice injected i.v. by DIL6-7,9 cells died 70–90 days post-injection, while control groups died 30–35 days after injection. Survival of mice injected i.f.p. with DIL6-7,9 ranged between 95–120 days post-injection (8/27 mice inoculated by DIL6-7 were non-metastatic after 120 days) as compared to 53–57 days survival in the control groups (not shown).

TABLE 2

Malignant phenotypes of D122 and IL-6 transfectants in syngeneic C57BL/6 mice

| Clone | Spontaneous metastasis Lung Weight (mg) | | Days till Amputation | | Experimental Metastasis Lung Weight (mg) | |
|---|---|---|---|---|---|---|
| | X ± S.D. | Med | X ± S.D. | | X ± S.D. | Med |
| D122 | 663 ± 356 | 565 | 30.5 ± 3.1 | | 849 ± 288 | 729 |
| DIL6-4 | 603 ± 328 | 562 | 31.1 ± 2.5 | | 1035 ± 300 | 943 |
| DIL6-2 | 237 ± 119 | 180 | 27.0 ± 1.0 | | 311 ± 167 | 234 |
| DIL6-7 | 183 ± 72 | 158 | 39.0 ± 2.4 | | 155 ± 20 | 151 |
| DIL6-9 | 175 ± 42 | 184 | 50.8 ± 6.2 | | 147 ± 21 | 140 |

Eight mice in each experimental group were inoculated i.f.p. with $2 \times 10^5$ cells (spontaneous metastasis) or i.v. with $5 \times 10^5$ cells (experimental metastasis). To evaluate spontaneous metastasis, tumor-bearing footpads were amputated when the tumor reached 8–9 mm diameter and mice were sacrificed 26 days post-amputation. To evaluate experimental metastasis, mice were sacrificed 35 days post inoculation.

To examine whether the inhibition in growth and metastatic spread is due only to inhibition in cell proliferation or if mechanisms related to the immune system are also involved, DIL6-4 and DIL6-9 cells were inoculated to syngeneic C57BL/6 mice and to a thymic, mature T cell-deficient CD1 Nu/Nu mice. Table 3 shows that the primary tumor growth of DIL6-9 is reduced as compared to DIL6-4 both in C57BL/6 and CD1 Nu/Nu mice, however the effect is more pronounced in the immune competent mice. Post-amputation survival of the DIL6-4-injected mice in CD1 Nu/Nu mice, while in the immune competent mice the difference was significant. Thus a role can be postulated for mature T cells in reduction of malignancy in IL-6 secreting cells.

TABLE 3

Malignant phenotype of D122-IL-6 transfectants in CD1 Nu/Nu and syngeneic C57BL/6 mice

| Clone | Mice | Days till amputation | | | Survival post amputation | | |
|---|---|---|---|---|---|---|---|
| | | X ± S.D. | Med | P | X ± S.D. | Med | P |
| DIL6-4 | C57BL/6 | 27.6 ± 1.6 | 27 | — | 28.0 ± 5.4 | 26 | — |
| DIL6-9 | C57BL/6 | 50.0 ± 3.5 | 49 | $<10^{-5}$ | 45.0 ± 8.8 | 44 | $10^{-3}$ |
| DIL6-4 | Nu/Nu | 31.3 ± 1.6 | 30 | — | 38.5 ± 10.4 | 38 | — |
| DIL6-9 | Nu/Nu | 45.3 ± 5.3 | 48 | $<10^{-3}$ | 40.2 ± 16.6 | 37 | $>0.5$ |

Ten mice in each C57BL/6 experimental group and seven mice in each Nu/Nu group were inoculated i.f.p. with $2 \times 10^5$ DIL6-4 or DIL6-9 cells. Tumor-bearing footpads were amputated when the tumor reached 8–9 mm diameter. The days until amputation and survival post-amputation were monitored. The differences in growth or survival of DIL6-9 compared to DIL6-4 in C57BL/6 or Nu/Nu mice were statistically analyzed by a wilcoxon rank sum test.

EXAMPLE 4

Immune mechanisms involved in the response to IL-6 transfectants IL-6 producing transfected cells, inactivated by irradiation and mycomycin-C, activate more cytotoxic lymphocytes (CTL) and recruit more macrophage than the non-producer cells. To test the involvement of cytotoxic T cells in the reduced malignancy of IL-6 transfectants, in vitro cytotoxic assays were performed as described in method (m) above with spleen cells of mice immunized as described in (1) above. Table 4 shows a representative assay. Immunization by IL-6 transfectants induced elevated levels of cytotoxic lymphocytes (CTLs) that killed more efficiently negative and positive IL-6 transfectants as compared to CTL induced by parental D122 cells. DIF1 (D122 cells transfected by gamma-IFN cDNA that expresses high levels of MHC class-I antigens) was a more sensitive target than IL-6 transfectants to these CTLs. YAC-I cells that are sensitive target to NK activity were not lysed by these CTLs.

TABLE 4

In vitro lytic activity of CTLs elicited by D122 and IL-6 transfectants

| Immunization | E/T ratio | Target | | | | |
|---|---|---|---|---|---|---|
| | | DIL6-4 | DIL6-7 | DIL6-9 | DIF1 | YAC-1 |
| D122 | 100:1 | 9 | 6 | 10 | 19 | 0 |
| | 50:1 | 10 | 6 | 6 | 14 | 0 |
| DIL6-7 | 100:1 | 19 | 21 | 19 | 25 | 0 |
| | 50:1 | 15 | 15 | 16 | 25 | 0 |
| DIL6-9 | 100:1 | 17 | 15 | 15 | 29 | 0 |
| | 50:1 | 14 | 10 | 13 | 24 | 0 |

Data shows percent specific lysis obtained with effect-to-target ratios of 100:1 and 50:1. Target cells, labeled with [$^{35}$S]-methionine, were reacted in a 16 hour assay with effector cells. The cytolytic activity on YAC-1 was determined after ten hours incubation. Error percentages were under 5% of the means of triplicates.

Since IL-6 is known to have pleiotropic effects on the immune system, it was also tested by the method (a) above whether IL-6 secreting tumor cells cause localization of macrophage at higher levels than parental cells. D122 or DIL6-7 cells after irradiation were injected i.p. Peritoneal exudates were removed on days 1, 3 and 5 post-injection and cells were stained for non-specific esterases.

FIG. 5 shows the macrophage percentage in peritoneal exudate cells of mice inoculated with D122 and DIL6-7 cells. Macrophage percentage is the percent of esterase positive cells in exudates (residual tumor cells omitted from count). Macrophage percentage in peritoneal exudates of naive mice is 5%. For each graph point six fields of 100 cells were counted and mean±s.d. were calculated. On day five, an elevation in peritoneal macrophage was observed both in D122 and DIL6-7 injected mice, however, D122 inoculated mice, 40% of peritoneal exudate cells stained for non-specific esterases, whereas 66% of peritoneal exudate cells were esterases positive in DIL6-7 inoculated mice.

EXAMPLE 5

Protective effects of IL-6 transfectants

Since IL-6 transfectants were shown above to stimulate host immune responses, it was next tested whether they can immunize against parental D122 cells. C57BL/6 mice were immunized three times i.p. with DIL6-2,7 and D122 cells as described in method (1) above. Ten days after the last immunization, mice were challenged i.v. with live D122 cells and survival of mice was monitored. FIG. 6 shows the survival curves of the mice preimmunized with irradiated and mitomycin-c treated tumor cells and inoculated i.v. with $5 \times 10^5$ living D122 cells. On day 160 6/7 mice immunized by DIL6-7 survived and were metastases free, while only 1/7 mice immunized with D122 survived after 120 days. Immunization by the low IL-6 expressor, DIL6-2, afforded only partial protection (3/7 mice survived without metastases after 120 days). This shows that preimmunization by IL-6 producing transfected cells protect mice against the highly metastatic D122 cells in the experimental metastasis model and prolong survival.

It was further tested whether IL-6 transfectants can protect tumor bearing mice against metastatic spread of parental cells in an "immunothreapy protocol". C57BL/6 male mice were inoculated i.f.p. with $2 \times 10^5$ living D122 cells and eleven days after inoculation, when palpable local tumors could be observed, mice were immunized weekly, for six weeks, with i.p. injection of $2 \times 10^6$ mitomycin-C treated D122 and DIL6-7 cells. The control group was inoculated with PBS. Immunization did not affect the growth of the primary tumors in the footpad. Primary tumors were amputated and mice were sacrificed 26 days post amputation when non-immunized mice died with heavy load of lung metastases. Immunization with D122 protected only marginally against metastatic spread of the local parental cells while immunization with positive IL-6 transfectant, DIL6-7, decreased significantly the amount of metastases (FIG. 7). Seven of 13 lungs weighed less then 271 mg., (normal lung weight of 4–5 month male mice is about 200 mg) and four of the seven were completely metastases free. When a similar experiment was performed in CD1 nude mice no therapeutic effects were observed. Metastatic growth of D122 cells was equally high in treated and non-treated nude mice (not shown).

pSVβ29 plasmid which carries a human IL-6 cDNA, and with pSV$_2$-neo plasmid. Fifteen neo-resistant clones were screened for secretion of IL-6 and one positive clone, FIL6-8, was chosen for further characterization. F10.9 cells were also transduced with virus stocks containing the pZL-IL6 retroviral expression vector (see methods) which were obtained from AM12 cells trans-infected with the vector and clones FIL6-23,25,29 and 30 clones were isolated. F10.9-neo is a pool of FIO.9 cells isolated after transduction with a virus stock containing the pZL retroviral vector. F10.9-neo cells are used as a control for the effect of infection and neomycin-resistant gene expression on the properties of F10.9 cells.

IL-6 levels in supernatants of IL-6 gene transferred were assayed using the IL-6 dependent murine hybridoma cell line B9. FIG. 8 shows that the secretion of the FIO.9 IL6-transfectant is significantly lower than the secretion of F10.9 IL6-transduced cells. A very low level of IL-6 (<0.03 IU/ml) was found in supernatant of F10.9 cells themselves.

EXAMPLE 7
Tumorigenicity and metastatic properties of FIO.9-IL6 gene transferred cells The IL-6 transfectant FIL6-8, grew similarly or even slightly faster than the negative control groups (FIO.9 and F10.9-neo), while the IL-6 transduced cells grew slightly slower than the control groups (Table 5). Spontaneous metastasis was evaluated 29 days post-amputation of tumor bearing footpads when parental F10.9 injected mice died with heavy loads of lung metastases. All IL6-transduced cells and the IL6-transfectant FIL6-8 were non-metastatic (occasionally lungs with 1–2 small metastases were observed). Experimental metastasis was evaluated 34 days after i.v. inoculation (Table 5). The very low IL-6 secretor, FIL6-8 showed high metastatic competence similarly to F10.9 and F10.9-neo cells while IL6-transduced cells showed a low-metastatic phenotype i.e. majority of mice in the group had non-metastatic lungs or lungs with 1–6 small metastases and 1⅜ mice had lungs with moderate or heavy loads of metastases. This heterogeneity in lung weights can be seen by the difference between average and median lung weights.

TABLE 5

Malignant phenotypes of F10.9 and IL6-secretors in syngeneic C57BL/6 mice

| | Days till amputation | | Spontaneous metastasis Lung weight (mg) | | Experimental metastasis Lung weight (mg) | | lung weight |
|---|---|---|---|---|---|---|---|
| Clone | X ± S.D. | Med | X ± S.D. | Med | X ± S.D. | Med | >200 mg |
| F10.9 | 33.0 ± 3.5 | 32 | 547 ± 342 | 523 | 513 ± 389 | 360 | 7/8 |
| F10.9-PAZ6 | 32.4 ± 1.1 | 32 | 512 ± 260 | 512 | 658 ± 336 | 620 | 8/8 |
| FIL6-8 | 30.8 ± 3.2 | 32 | 133 ± 8 | 131 | 510 ± 232 | 445 | 8/8 |
| FIL6-23 | 36.2 ± 2.7 | 35 | 152 ± 27 | 147 | 278 ± 236 | 172 | 3/8 |
| FIL6-25 | 35.5 ± 1.2 | 35 | 170 ± 73 | 142 | 207 ± 75 | 188 | 3/8 |
| FIL6-29 | 35.8 ± 2.7 | 35 | 159 ± 16 | 160 | 175 ± 57 | 151 | 1/8 |
| FIL6-30 | 37.0 ± 3.1 | 38 | 141 ± 14 | 149 | 247 ± 157 | 185 | 3/8 |
| K1 | | | | | 165 ± 7 | 164 | 0/8 |

Thus IL-6 transfectants induced protective mechanisms in vivo that protected recipients from metastatic spread of parental highly metastatic cells.

EXAMPLE 6
Transfection and retroviral transduction of IL-6 cDNA into F10.9 cells F10.9 is a low-immunogenic and high metastatic clone of B16-F10 melanoma. F10.9 cells were cotransfected with Eight mice in each experimental group were inoculated i.f.p. with $2 \times 10^5$ cells (spontaneous metastasis) or i.v. with $5 \times 10^4$ cells (experimental metastasis). To evaluate spontaneous metastasis tumor bearing footpads were amputated when the tumor reached 8–9 mm diameter and mice were sacrificed 29 days post amputation. To evaluate experimental metastasis mice were sacrificed 34 day post inoculation. K1 is a positive $K^b$ transfectant of F10.9 clone. * Footpads of 6 out of 8 mice did not grow.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

What is claimed is:

1. An anti-tumor pharmaceutical composition comprising tumor cells from a patient wherein a nucleic acid construct comprising a DNA sequence encoding human IL-6 operably linked to a promoter has been inserted into said cells, and wherein in said cells further have been inactivated to inhibit cell division, and a pharmaceutically acceptable carrier.

2. The pharmaceutical composition according to claim 1, wherein said tumor cells are metastatically competent.

3. The pharmaceutical composition according to claim 1, wherein said tumor cells are not metastatically competent.

4. The pharmaceutical composition according to claim 1, wherein said nucleic acid construct has been introduced by an expression vector and wherein the introduction results in constitutive production of human IL-6 in in vivo.

5. The pharmaceutical composition according to claim 1, wherein said nucleic acid construct has been introduced by a retroviral vector and wherein the introduction results in constitutive production of human IL-6 in in vivo.

6. The pharmaceutical composition according to claim 1, wherein said cells have been transfected with an expression vector comprising a DNA sequence encoding human IL-6 operably linked to a promoter and wherein the expression of said DNA sequence results in constitutive production of human IL-6 in in vivo.

7. The pharmaceutical composition according to claim 1, wherein said cells have been transfected with a retroviral vector comprising a DNA sequence encoding human IL-6 operably linked to a promoter and wherein the expression of said DNA sequence results in constitutive production of human IL-6 in in vivo.

8. The pharmaceutical composition according to claim 1, wherein said inactivation is by at least one treatment selected from the group consisting of irradiation and mitomycin C.

9. The pharmaceutical composition according to claim 1, comprising from about $1 \times 10^6$ to about $1 \times 10^9$ cells comprising the inserted nucleic acid construct.

10. The pharmaceutical composition according to claim 1 which has been formulated for injection.

11. An anti-tumor pharmaceutical composition comprising:
   tumor cells from a patient, wherein said tumor cells are a mixed population of cells with and without metastatic competence,
   said cells being transfected by a DNA sequence encoding human IL-6 operably linked to a promoter, wherein the transfection results in the constitutive production of human IL-6 in vivo, and said cells inactivated by treatment selected from at least one of the group consisting of y-irradiation, X-irradiation and mitomycin C.

12. A method of treatment of a patient suffering from cancer comprising administering to said patient a pharmaceutical composition according to claim 1 in an amount sufficient to inhibit tumor metastasis.

13. A method for the treatment of a patient suffering from a malignant solid tumor, comprising the steps of:
   a) removing tumor cells from the patient;
   b) dispersing said cells in a medium;
   c) inserting into said cells a nucleic acid construct comprising a DNA sequence encoding human IL-6 operably linked to a promoter;
   d) selecting for those cells which express human IL-6 into the medium;
   e) inactivating secreting cells with y or X-irradiation and/or treatment with mitomycin C; and
   f) administering an effective amount of the inactivated, human IL-6 secreting cells into a patient such that an antitumor response is induced in said patient and the response results in the inhibition of metastasis of said solid tumor.

14. The method according to claim 13, wherein said step of selecting comprises selecting from the group consisting of cloned positive human IL-6 producing cells, mixtures of positive and negative human IL-6 producing cells and low human IL-6 producing cells.

* * * * *